(12) United States Patent
Reiter et al.

(10) Patent No.: US 8,404,116 B2
(45) Date of Patent: Mar. 26, 2013

(54) SAFETY INSERT FOR EXTRA-CORPOREAL CIRCUITS

(75) Inventors: Reinhold Reiter, Crema (IT); Paolo Stabilini, Romanengo (IT)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 13/147,850

(22) PCT Filed: Mar. 3, 2010

(86) PCT No.: PCT/EP2010/052659
§ 371 (c)(1),
(2), (4) Date: Aug. 4, 2011

(87) PCT Pub. No.: WO2010/100177
PCT Pub. Date: Sep. 10, 2010

(65) Prior Publication Data
US 2011/0284449 A1   Nov. 24, 2011

(30) Foreign Application Priority Data
Mar. 6, 2009  (EP) .................................. 09154485

(51) Int. Cl.
*B01D 35/14* (2006.01)
*B01D 61/18* (2006.01)
*B01D 35/30* (2006.01)

(52) U.S. Cl. ............ 210/232; 210/240; 210/321.6
(58) Field of Classification Search ........... 210/232, 210/240, 321.6
See application file for complete search history.

(56) References Cited

U.S. PATENT DOCUMENTS
6,168,653 B1   1/2001  Myers

FOREIGN PATENT DOCUMENTS
| EP | 0 652 018 | 5/1995 |
|----|-----------|--------|
| EP | 0 878 628 | 11/1998 |
| EP | 1 097 725 | 5/2001 |
| EP | 1 464 359 | 10/2004 |
| WO | WO 2004/082732 | 9/2004 |

*Primary Examiner* — John Kim
(74) *Attorney, Agent, or Firm* — Jacobson Holman PLLC

(57) ABSTRACT

A transducer protector for use in an extra-corporeal circuit includes a first half-shell, a second half-shell, and a hydrophobic semi-permeable membrane enclosed between the half-shells. The first half-shell includes a first tubular connector with a seat having a substantially cylindrical shape and defining an axis X. The second half-shell includes a second tubular connection configured for connection to a transducer. The seat receives an end of a branch pipe from the circuit. The end defines a front surface substantially in the form of an annulus that is insertable inside the seat, which has one or more abutments that form a support for the front surface of the end to define a stop for the end. The abutment defines at least one radially outer cavity and provides a partial support for the front surface of the end. The cavity provides at least one radially outer zone of the annulus without support.

8 Claims, 7 Drawing Sheets

SAFETY INSERT FOR EXTRA-CORPOREAL CIRCUITS

CROSS-REFERENCE TO RELATED APPLICATION

This is a national stage of PCT/EP10/052659 filed Mar. 3, 2010 and published in English, which claims the priority of European number 09154485.8 filed Mar. 6, 2009, hereby incorporated by reference.

BACKGROUND OF THE INVENTION

1. Field of Invention

The invention relates to a safety insert for extra-corporeal circuits, in particular a seat formed in the insert for receiving a pipe.

2. Description of the Prior Art

In therapeutic treatment which requires an extra-corporeal circulation system, such as haemodialysis, the arterial and venous pressure in the extra-corporeal circuit must be constantly monitored. This is achieved in a manner known per se by means of pressure transducers connected to the main circuit via suitable branch pipes. In an equally known manner, a safety insert or transducer protector is positioned between the pipe and the pressure transducer in order to avoid any possible contact between the patient's blood and the machine (artificial kidney). In fact, the extra-corporeal circuit is made of disposable material, while the artificial kidney as a whole must, of necessity, be continuously reused.

The transducer protector is formed, in a manner known per se, by means of two plastic half-shells enclosing between them a hydrophobic gas permeable membrane. Each of the two half-shells comprises a tubular connector. A first tubular connector is designed to be connected to the branch pipe, while the other tubular connector is designed to be connected to the pressure transducer.

In particular, during assembly of the disposable material, the branch pipe is dipped in a solvent and manually inserted inside the first tubular connector of the transducer protector so as to obtain secure bonding together of the two parts.

This solution, although widely used, is not defect-free. In fact, the use of an excessive quantity of solvent may easily result in the contamination of the hydrophobic membrane and cause consequent damage thereto. Obviously, the correct assembly procedure requires the removal of any excess solvent in order to limit the possibility of this occurring.

The structure of the known transducer protectors therefore has a minimum safety margin which is essentially dependent on the procedure and the degree to which it is complied with by the operator.

The Applicant expressly conducted a specific series of tests to investigate these problems. In particular, 194 pairs of pipes and transducer protectors of the known type were assembled. With each of the 194 pairs the aforementioned assembly operation was systematically conducted in a manner which deliberately did not comply with the procedure. The result of the tests was that the failure to remove the excess solvent resulted in contamination of the membrane in as many as 106 of the 194 cases, i.e. in more than 54% of the total number of cases. The above therefore shows how the transducer protector of the known type proves to be reliable only if used in strict compliance with the procedures indicated. It would therefore be highly desirable to provide a transducer protector able to ensure a greater safety margin, in particular, a safety margin able to prevent contamination of the membrane even in the case where the operator commits errors during application of the procedure or in the case where he/she is unable or considers it unnecessary to adhere rigorously to the procedure.

Safety inserts of the type considered above are described in detail in the documents EP 0 652 018, EP 1 097 725 and EP 0 878 628.

SUMMARY OF THE INVENTION

The object of the present invention is therefore to solve at least partially the drawbacks identified in connection with the safety inserts of the known type.

The aim of the present invention is to provide a transducer protector for extra-corporeal circuits which has a greater intrinsic safety margin. In particular, the aim of the present invention is to provide a transducer protector which has a safety margin such as to be able to tolerate also a bonding procedure which is not rigorously complied with.

The abovementioned object and aims are achieved by a safety insert as described herein.

BRIEF DESCRIPTION OF THE DRAWINGS

The characteristic features and further advantages of the invention will emerge more clearly from the following description provided below, of a number of examples of embodiment, described by way of a non-limiting example, with reference to the accompanying drawings in which.

DETAILED DESCRIPTION OF THE PREFERRED EMBODIMENTS

Figure 2:
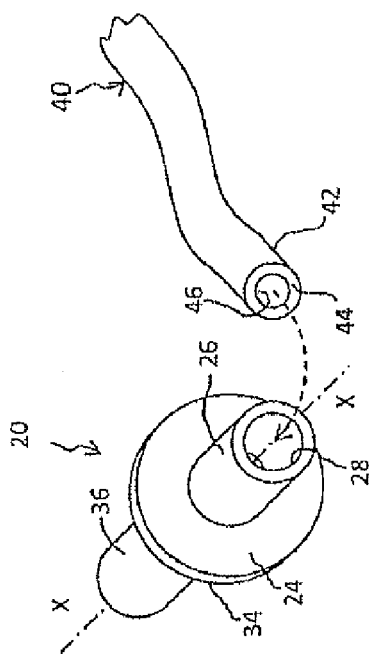
FIG. 2 shows in schematic form a detail of the connection between a branch pipe and a generic transducer protector.
Figure 1:
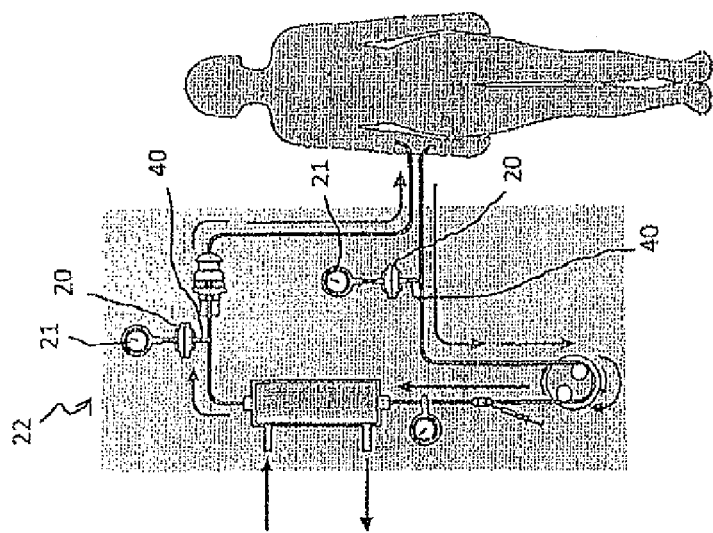
FIG. 1 shows in schematic form an extra-corporeal circuit used in therapeutic treatment.
Figure 3:
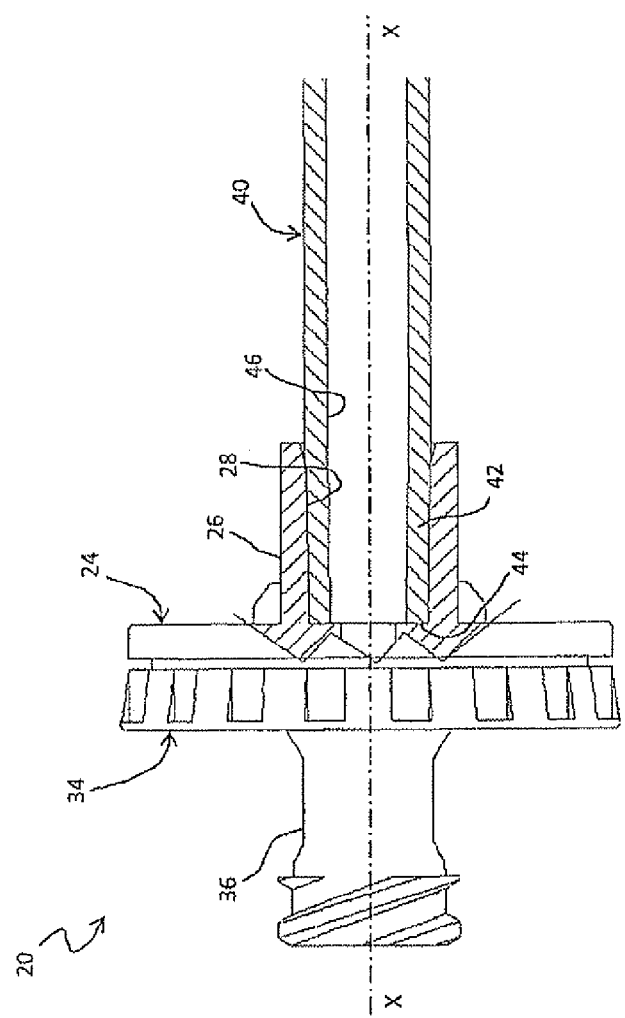
FIG. 3 shows a partially cross-sectioned schematic view of a transducer protector of the known type.
Figure 5:
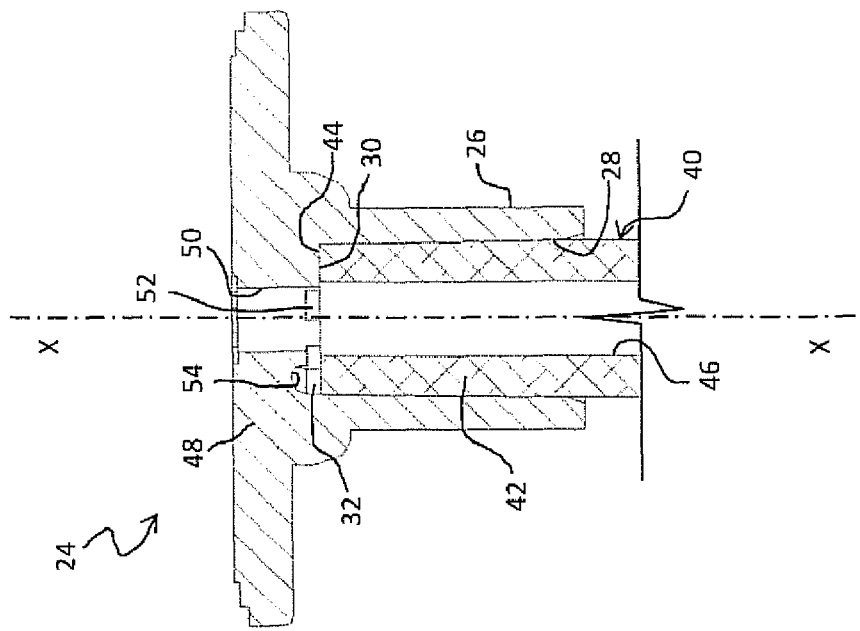
FIG. 5 shows a cross-sectional view of a transducer protector according to the invention.
Figure 4:
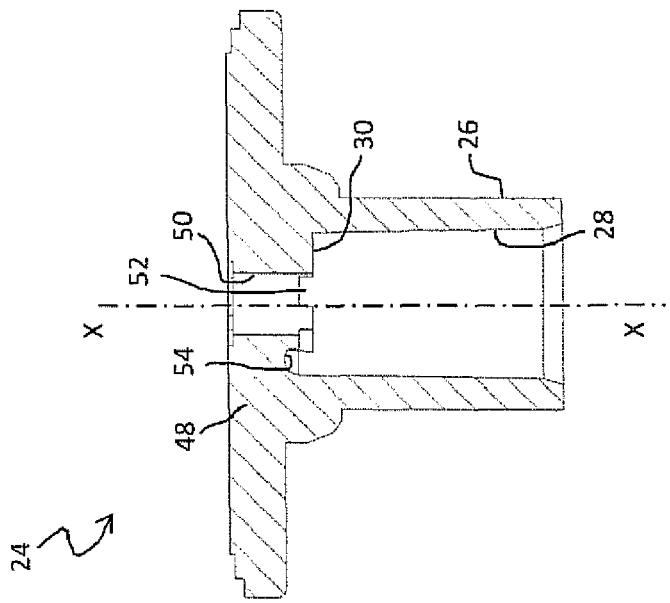
FIG. 4 shows a cross-sectional perspective view of a detail of a transducer protector according to the invention.
Figure 7:
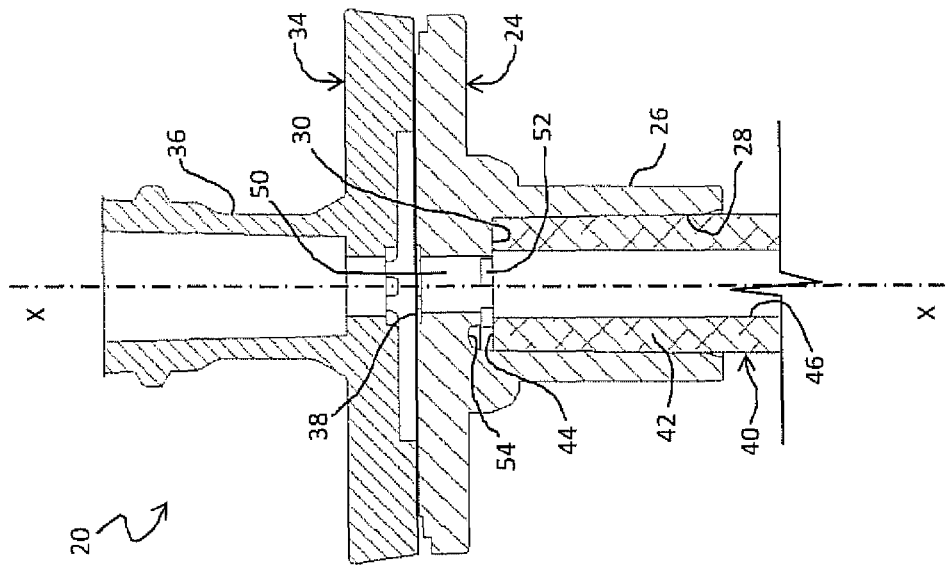
FIG. 7 shows a cross-sectional view of a detail of a transducer protector according to the invention.
Figure 6:
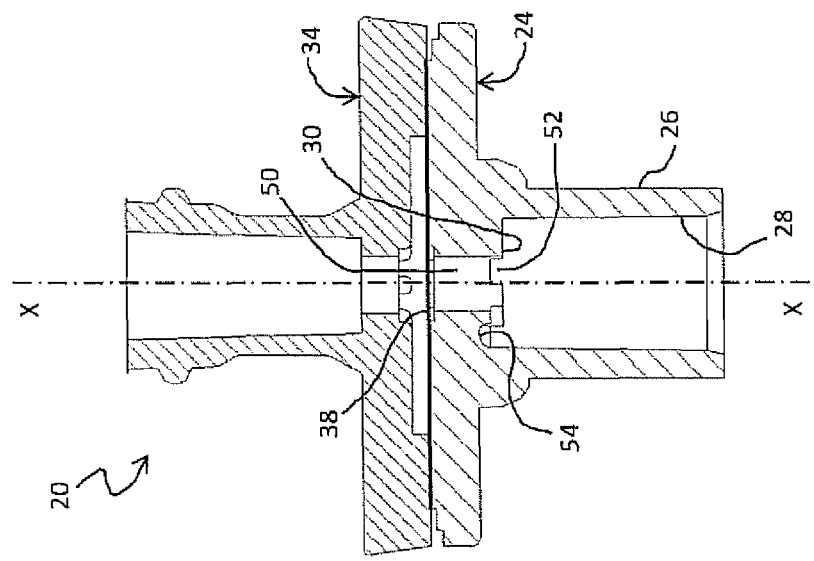
FIG. 6 shows a cross-sectional view of a transducer protector according to the invention and a pipe connected thereto.
Figure 8:
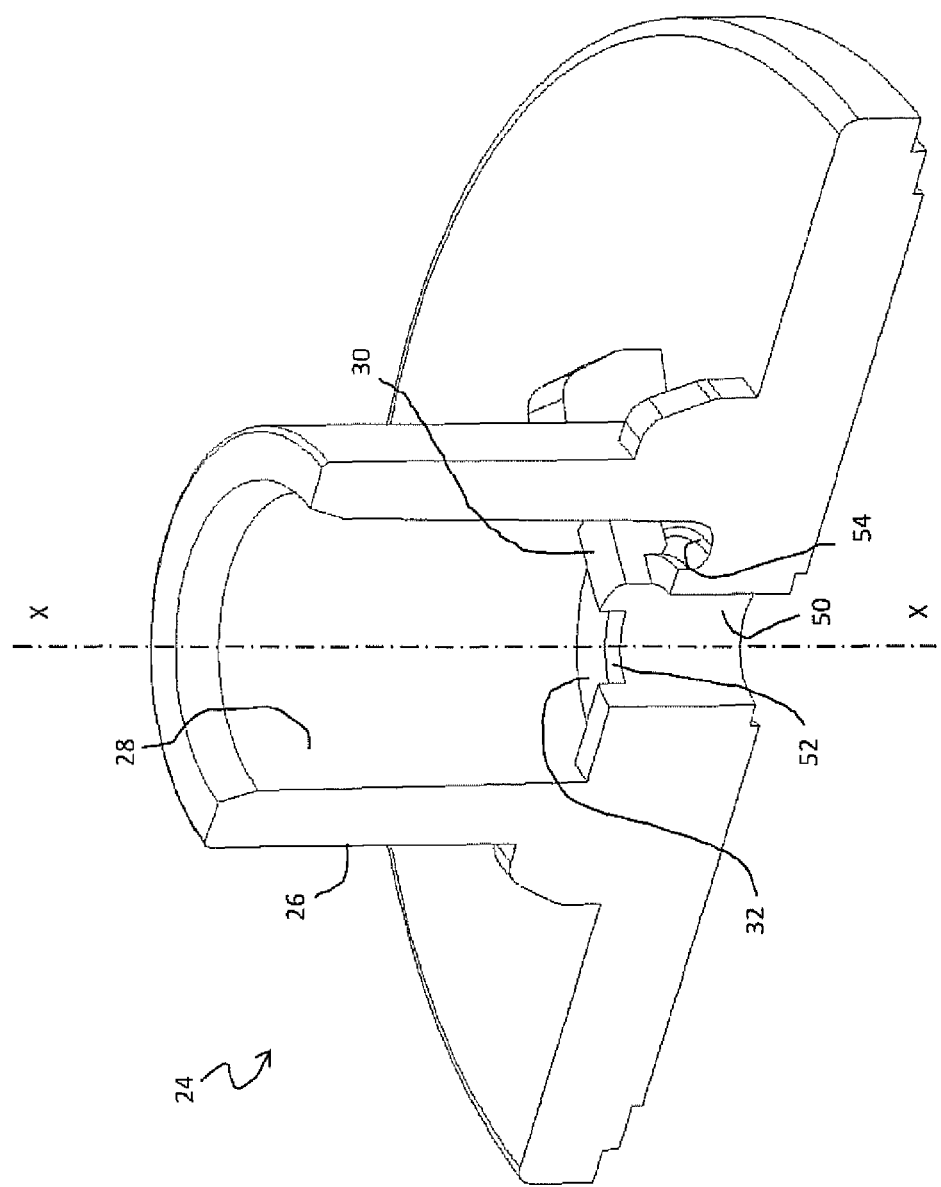
FIG. 8 shows a cross-sectional view of a detail of a transducer protector according to the invention and a pipe connected thereto.
Figure 9:
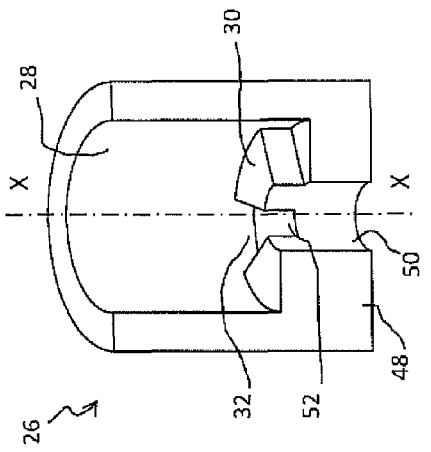
FIG. 9 shows a cross-sectional view along the line IX-IX in FIG. 10.
Figure 10:
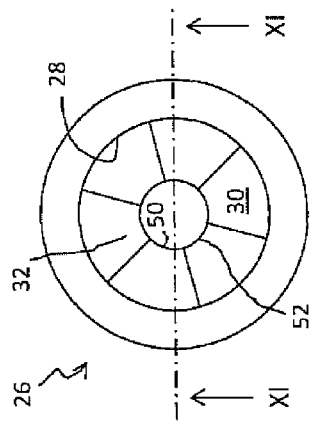
FIG. 10 shows in schematic form a different embodiment of the first connector of the transducer protector according to the invention.
Figure 11:
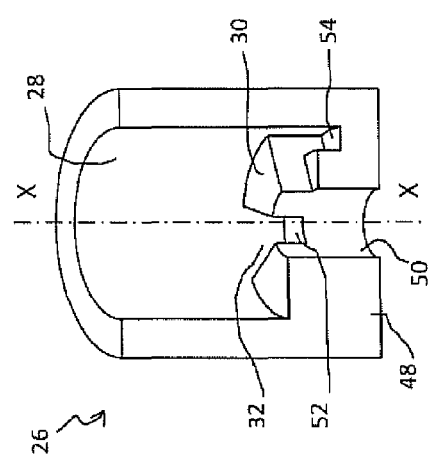
FIG. 11 shows a cross-sectional view along the line XI-XI in FIG. 12.
Figure 12:
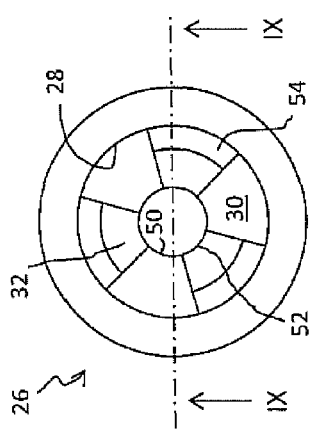
FIG. 12 shows in schematic form a different embodiment of the first connector of the transducer protector according to the invention.
Figure 13:
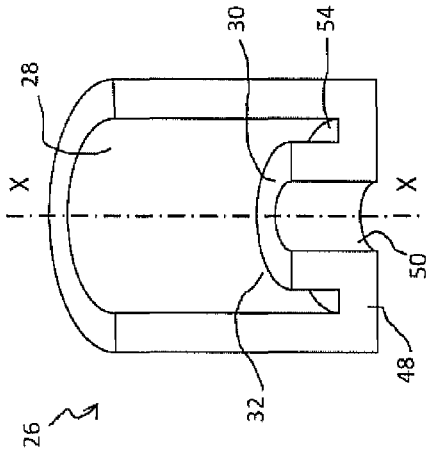
FIG. 13 shows a cross-sectional view along the line XIII-XIII in FIG. 14.
Figure 14:
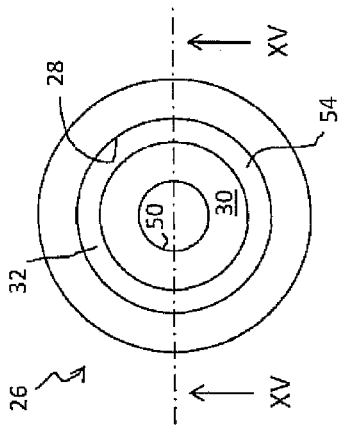
FIG. 14 shows in schematic form a different embodiment of the first connector of the transducer protector according to the invention.

Further scope of applicability of the present invention will become apparent from the detailed description given hereinafter. However, it should be understood that the detailed description and specific examples, while indicating preferred embodiments of the invention, are given by way of illustration only, since various changes and modification within the spirit and scope of the invention will become apparent to those skilled in the art from this detailed description.

The present invention relates to a safety insert or transducer protector indicated in its entirety by 20. The transducer protector 20 is designed to be used in an extra-corporeal circuit 22 and comprises a first half-shell 24, a second half-shell 34 and a hydrophobic semi-permeable membrane 38 enclosed between the two half-shells 24 and 34. The first half-shell 24 comprises a first tubular connector 26 in turn comprising a seat 28 having a substantially cylindrical shape and defining an axis X. The second half-shell 34 comprises a second tubular connector 36 designed for connection to a transducer 21. The seat 28 is designed to receive an end 42 of a branch pipe 40 from the extra-corporeal circuit 22. The end 42 defines a front surface substantially in the form of an annulus 44 and can be inserted inside the seat 28 in the axial direction along the axis X. The seat 28 comprises one or more abutments 30 designed to form a support for the front surface of the end 42 so as to define a limit stop in the axial direction for the end 42. The at least one abutment 30 defines at least one radially outer cavity 32, so as to define a partial support for the annulus 44 of the front surface of the end 42. The cavity 32 is designed to leave at least one radially outer zone of the annulus 44 without support.

In other words, the abutments 30 do not define a support area corresponding perfectly to the annulus 44 of the front surface of the end 42. The support area defined by the abutments 30 is not intended for the entire annulus 44 but only for some zones, preferably radially inner zones.

Here and below, the expressions "axial", "radial" and "circumferential" (or "tangential") are defined in relation to the axis X. In particular, "axial" is understood as meaning the direction of a straight line parallel to X; "radial" is understood as meaning the direction of a half-line originating on X and perpendicular thereto; "circumferential" (or "tangent") is understood as meaning the direction of a (straight line tangential to a) circumference centred on X and lying in a plane perpendicular thereto.

Here and below, with reference to the transducer protector, the terms "forward", "front" and the like define positions relatively close to the inlet of the first tubular connector 26 and far from the inlet of the second tubular connector 36. On the other hand, the terms "backward", "rear" and the like define positions relatively close to the inlet of the second tubular connector 36 and far from the inlet of the first tubular connector 26.

In accordance with the embodiments of the accompanying figures, the seat 28 comprises a through-hole 50 which passes through the entire first half-shell 24. The seat 28 also comprises an end wall 48 through which the through-hole 50 extends so as to ensure the hydraulic continuity between the lumen 46 of the pipe 40 and the transducer 21, through the membrane 38 and the second half-shell 34. Each abutment 30 defines a support area situated axially further forward than the end wall 48 of the seat 28.

In accordance with the embodiments shown in FIGS. 4 to 14, the seat 28 comprises a plurality of abutments which extend in a substantially radial direction. These abutments 30 are tangentially spaced from one another so that a cavity 32 is formed between each pair of tangentially successive abutments 30. Each of these cavities 32 extends radially in a manner substantially similar to that of the abutments 30. In this case, therefore, the support area defined for the annulus 44 is circumferentially discontinuous.

In accordance with these and other embodiments, the cavities 32 define radial inner openings 52 which open out into the central channel defined by the hole 50 and by the lumen 46 of the pipe 40 when the end 42 is inserted.

In accordance with other embodiments, the seat 28 comprises at least one abutment 30 which extends in the circumferential direction. This abutment 30 defines at least one annular cavity 32 arranged radially more externally than the abutment 30. In some cases (not shown) a plurality of concentric abutments 30 extend in a circumferential direction and define a plurality of cavities 32 which are in turn concentric.

Figure 15:
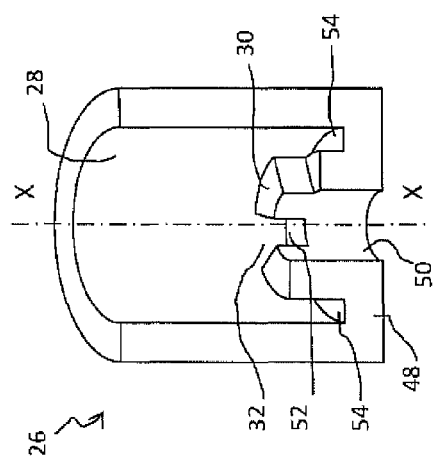
FIG. 15 shows a cross-sectional view along the line XV-XV in FIG. 16.
Figure 16:
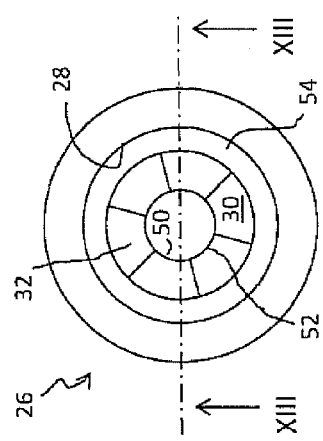
FIG. 16 shows in schematic form a different embodiment of the first connector of the transducer protector according to the invention.

In accordance with the embodiment according to FIGS. 15 and 16, the seat 28 comprises a single abutment 30 which extends in the circumferential direction. This abutment 30 defines an annular cavity 32 which is arranged radially more externally than the abutment. In this case, therefore, the support area defined for the annulus 44 is circumferentially continuous, but limited to the radially inner zone only, while the radially outer zone of the annulus 44 remains without support.

In accordance with certain embodiments, for example those shown in FIGS. 4 to 10 and 13 to 16, the seat also comprises a groove 54 designed to perform a buffer function. The groove 54 is therefore sunk in the end wall 48 of the seat 28, providing a free space situated axially even further back than, for example, the radial openings 52.

With use of a transducer protector according to the invention it is possible to protect the membrane 38 from contamination with solvent, while continuing to use the same procedure used in the prior art. In particular, according to said procedure, the end 42 of the pipe 40 must be dipped in the solvent and inserted into the seat 28. The particular configuration of the seat 28 prevents the pressure exerted by the operator from compressing any excess solvent such that it seeps into the hole 50 and reaches the membrane 38. In fact, the at least one abutment 30 provides the support necessary for defining for the pipe 40 a limit stop situated axially further forward than the end wall 48 of the seat 28. At the same time the presence of at least one cavity 32 ensures that zones of the annulus 44 are without support and therefore free from any pressure. In these zones the pressure acting on any excess solvent may be discharged.

Moreover, the radial inner openings 52, where present, ensure that the excess solvent remains in contact with the air circulating inside the lumen 46 of the pipe 40. In this way the excess solvent may evaporate without therefore constituting a danger for the membrane 38.

Finally, the groove 54, where present, ensures that the excess solvent is collected and confined in a space situated axially further back than the end wall 48 of the seat 28. In this way it is possible to eliminate the—albeit remote—risk of the excess solvent, when not yet evaporated, seeping through the radial openings 52.

The Applicant expressly conducted a specific series of tests to determine the benefits obtained by means of the transducer protector according to the invention. In particular, 145 pairs of pipes and transducer protectors according to the invention (shown in the embodiment of FIGS. 4 to 8) were assembled. In each of the 145 pairs the aforementioned assembly operation was systematically conducted in a manner which deliberately did not comply with the procedure. The result of the tests was that the failure to remove the excess solvent never resulted in contamination of the membrane, i.e. in 0% of the total number of cases. The above therefore shows how the transducer protector according to the invention proves to be reliable even when used without rigorously complying with the procedures indicated.

With regard to the embodiments of the transducer protector described above, the person skilled in the art may, in order to satisfy specific requirements, make modifications to and/or replace elements described with equivalent elements, without thereby departing from the scope of the accompanying claims.

What is claimed is:

1. A safety insert or an extra-corporeal circuit, comprising:
   a first half-shell including a first tubular connector with a seat having a substantially cylindrical shape and defining an axis X;
   a second half-shell including a second tubular connector configured for connection to a transducer; and
   a hydrophobic semi-permeable membrane enclosed between the first half-shell and the second half shell, the seat being configured to receive an end of a branch pipe from the extra-corporeal circuit, with said end defining a front surface substantially configured as an annulus and being insertable inside the seat in an axial direction along the axis X,
   the seat including a plurality of abutments extending in a substantially radial direction and being tangentially spaced from one another so as to form a support for the front surface of the end and define a limit stop in the axial direction for the end, and
   the abutments defining a partial support for the annulus of the front surface of the end and defining at least one radially outer cavity configured to leave at least one radially outer zone of the annulus without support.

2. The insert according to claim 1, wherein the cavity is provided between each pair of tangentially successive abutments.

3. The insert according to claim 1, wherein the cavity extends radially in a manner substantially similar to that of the abutments.

4. The insert according to claim 1, wherein the cavity defines radial inner openings which open out into a central through-hole.

5. The insert according to claim 1, wherein at least one of the abutments extends in the circumferential direction.

6. The insert according to claim 5, wherein the at least one of the abutments defines at least one annular cavity which is arranged radially more externally than the abutment.

7. The insert according to claim 1, wherein the seat includes a groove configured to perform a buffer function.

8. An extra-corporeal circuit comprising:
   at least one branch pipe;
   at least one transducer, and
   at least one safety insert connected to the branch pipe and to the transducer,
   said safety insert including
   a first half-shell including a first tubular connector with a seat having a substantially cylindrical shape and defining an axis X,
   a second half-shell including a second tubular connector configured for connection to the transducer, and
   a hydrophobic semi-permeable membrane enclosed between the first half-shell and the second half-shell,
   the seat being configured to receive an end of the branch pipe from the extra-corporeal circuit, with said end defining a front surface substantially configured as an annulus and being insertable inside the seat in an axial direction along the axis X,
   the seat including a plurality of abutments extending in a substantially radial direction and being tangentially spaced from one another so as to form a support for the front surface of the end and define a limit stop in the axial direction for the end, and
   the abutments defining a partial support for the annulus of the front surface of the end and defining at least one radially outer cavity configured to leave at least one radially outer zone of the annulus without support.

* * * * *